United States Patent
Jiang et al.

(10) Patent No.: US 10,458,903 B2
(45) Date of Patent: Oct. 29, 2019

(54) METHOD AND APPARATUS FOR MONITORING A LEVEL OF A GASEOUS SPECIES OF INTEREST

(71) Applicant: KONINKLIJKE PHILIPS N.V., Eindhoven (NL)

(72) Inventors: Zhi-Xing Jiang, Southbury, CT (US); Anthony Pierry, Plantsville, CT (US)

(73) Assignee: Koninklijke Philips N.V., Eindhoven (NL)

( * ) Notice: Subject to any disclaimer, the term of this patent is extended or adjusted under 35 U.S.C. 154(b) by 1014 days.

(21) Appl. No.: 14/761,506

(22) PCT Filed: Jan. 14, 2014

(86) PCT No.: PCT/IB2014/058259
§ 371 (c)(1),
(2) Date: Jul. 16, 2015

(87) PCT Pub. No.: WO2014/111847
PCT Pub. Date: Jul. 24, 2014

(65) Prior Publication Data
US 2015/0338340 A1    Nov. 26, 2015

Related U.S. Application Data

(60) Provisional application No. 61/753,484, filed on Jan. 17, 2013.

(51) Int. Cl.
*A61B 5/05* (2006.01)
*G01N 21/31* (2006.01)
(Continued)

(52) U.S. Cl.
CPC ......... *G01N 21/3151* (2013.01); *A61B 5/082* (2013.01); *G01J 3/108* (2013.01);
(Continued)

(58) Field of Classification Search
CPC ... G01N 2021/3181; G01N 2021/8578; G01N 21/3151; G01N 33/497; G01N 21/359;
(Continued)

(56) References Cited

U.S. PATENT DOCUMENTS

| | | |
|---|---|---|
| 4,899,053 A | 2/1990 | Lai et al. |
| 5,942,755 A | 8/1999 | Dreyer |

(Continued)

FOREIGN PATENT DOCUMENTS

| | | |
|---|---|---|
| CN | 101089609 A | 12/2007 |
| CN | 102027344 A | 4/2011 |

(Continued)

*Primary Examiner* — Mark D Remaly
(74) *Attorney, Agent, or Firm* — Michael W. Haas

(57) ABSTRACT

A gas measurement detector includes first and second sources emitting mid- and near-infrared electromagnetic radiation respectively; source optics combining mid- and near-infrared electromagnetic radiation emitted by the first and second sources into a coaxial beam directed across a flow path of a flow of breathable gas; sensor optics dividing electromagnetic radiation in the coaxial beam that has traversed the flow path into first radiation that includes mid-infrared electromagnetic radiation and second radiation that includes near-infrared electromagnetic radiation; first and second radiation sensors generating output signals conveying information related to a parameter of the mid-infrared electromagnetic radiation in the first radiation and a parameter of the near-infrared electromagnetic radiation in the second radiation, respectively; and a processor determining a level of a gaseous molecular species based on the output signals with the output signals generated by the second radiation sensor compensating optical loss through the flow path.

20 Claims, 2 Drawing Sheets

(51) Int. Cl.
    *G01N 33/497*      (2006.01)
    *G01N 21/3504*      (2014.01)
    *G01J 3/10*      (2006.01)
    *G01N 21/27*      (2006.01)
    *G01N 21/359*      (2014.01)
    *G01J 3/28*      (2006.01)
    *G01J 3/42*      (2006.01)
    *A61B 5/08*      (2006.01)
    *G01N 21/85*      (2006.01)
    *A61M 16/10*      (2006.01)

(52) U.S. Cl.
    CPC . G01J 3/28 (2013.01); G01J 3/42 (2013.01); G01N 21/274 (2013.01); G01N 21/3504 (2013.01); G01N 21/359 (2013.01); G01N 33/497 (2013.01); *A61B 5/0507* (2013.01); *A61M 2016/102* (2013.01); *A61M 2016/103* (2013.01); *A61M 2205/3313* (2013.01); *G01N 2021/3181* (2013.01); *G01N 2021/8578* (2013.01); *G01N 2201/062* (2013.01); *G01N 2201/0612* (2013.01)

(58) Field of Classification Search
    CPC ............. G01N 21/3504; G01N 21/274; G01N 2201/0612; G01N 2201/062; A61B 5/082; A61B 5/0507; G01J 3/42; G01J 3/28; G01J 3/108; A61M 2016/103; A61M 2205/3313

See application file for complete search history.

(56) References Cited

U.S. PATENT DOCUMENTS

| | | | |
|---|---|---|---|
| 8,365,730 B2 * | 2/2013 | Baker, Jr. | A61B 5/0205 128/200.24 |
| 2004/0010186 A1 * | 1/2004 | Kimball | A61B 5/02133 600/310 |
| 2004/0212804 A1 * | 10/2004 | Neff | G01J 3/433 356/435 |
| 2008/0315102 A1 | 12/2008 | Weidmann | |
| 2010/0078563 A1 | 4/2010 | Haveri et al. | |
| 2015/0268159 A1 | 9/2015 | Tabaru et al. | |

FOREIGN PATENT DOCUMENTS

| | | | |
|---|---|---|---|
| JP | H0989765 A | 4/1997 | |
| JP | 2012509493 A | 4/2012 | |
| JP | 2012108095 A | 6/2012 | |
| JP | 2013003511 A | 1/2013 | |
| WO | 2012153209 A1 | 11/2012 | |
| WO | WO 2012153209 A1 * | 11/2012 | ............ G01J 3/108 |

* cited by examiner

METHOD AND APPARATUS FOR MONITORING A LEVEL OF A GASEOUS SPECIES OF INTEREST

This application is a national stage application under 35 U.S.C. § 371 of International Application No. PCT/1132014/058259 filed on Jan. 14, 2014 and published in the English language on Jul. 24, 2014 as International Publication No. WO 2014/111847 A1, which claims priority to U.S. Application No. 61/753,484 filed on Jan. 17, 2013, the entire disclosures of which are incorporated herein by reference.

BACKGROUND

1. Field

The present disclosure pertains to a method and apparatus for enhanced gas measurement by infrared spectroscopy through implementing a near-infrared electromagnetic radiation source to generate reference electromagnetic radiation.

2. Description of the Related Art

Systems that perform the measurement of gas levels based on the measurement of infrared electromagnetic radiation that has passed through the gas are known. Typically, in such systems that measure gas levels in a respiratory circuit, electromagnetic radiation emitted by an individual radiation source in the mid-infrared range is used for both measurement and a reference to compensate for optical loss (e.g., scattering, blockage, and/or other loss). These devices typically employ two separate sensors for measurement intensity in the mid-infrared range.

SUMMARY

Accordingly, one or more aspects of the present disclosure relate to a detector (10) configured to monitor a level of a gaseous molecular species within a flow of breathable gas. In some embodiments, the detector comprises a first source, a second source, source optics, sensor optics, a first radiation sensor, a second radiation sensor, and a processor. The first source is configured to emit mid-infrared electromagnetic radiation. The second source is configured to emit near-infrared electromagnetic radiation. The source optics are configured to combine mid-infrared electromagnetic radiation emitted by the first source and near-infrared electromagnetic radiation emitted by the second source into a coaxial beam, and to direct the coaxial beam across a flow path of a flow of breathable gas that communicates with an airway of a subject. The sensor optics are configured to receive electromagnetic radiation in the coaxial beam that has traversed the flow path, and to divide the received electromagnetic radiation into first radiation that includes mid-infrared electromagnetic radiation and second radiation that includes near-infrared electromagnetic radiation. The first radiation sensor is configured to receive the first radiation, and to generate output signals conveying information related to a parameter of the mid-infrared electromagnetic radiation in the first radiation. The second radiation sensor is configured to receive the second radiation, and to generate output signals conveying information related to a parameter of the near-infrared electromagnetic radiation in the second radiation. The processor is configured to determine a level of a gaseous molecular species within the flow of breathable gas in the flow path based on the output signals generated by the first radiation sensor and the second radiation sensor such that the output signals generated by the second radiation sensor are implemented to compensate optical loss through the flow path.

Yet another aspect of the present disclosure relates to a method of monitoring a level of a gaseous molecular species within a flow of breathable gas with a detector that includes a first source, a second source, source optics, sensor optics, a first radiation sensor, a second radiation sensor, and a processor. The method comprises emitting mid-infrared electromagnetic radiation from the first source; emitting near-infrared electromagnetic radiation from the second source; combining, with the source optics, mid-infrared electromagnetic radiation emitted by the first source and near-infrared electromagnetic radiation emitted by the second source into a coaxial beam; directing, with the source optics, the coaxial beam across a flow path of the flow of breathable gas that communicates with an airway of a subject; dividing, with the sensor optics, electromagnetic radiation in the coaxial beam that has traversed the flow path into first radiation that includes mid-infrared electromagnetic radiation and second radiation that includes near-infrared electromagnetic radiation; generating, with the first radiation sensor, output signals conveying information related to a parameter of the mid-infrared electromagnetic radiation in the first radiation; generating, with the second radiation sensor, output signals conveying information related to a parameter of the near-infrared electromagnetic radiation in the second radiation; and determining, by the processor, a level of a gaseous molecular species within the flow of breathable gas in the flow path based on the output signals generated by the first radiation sensor and the second radiation sensor such that the output signals generated by the second radiation sensor are implemented to compensate optical loss through the flow path.

Still another aspect of present disclosure relates to a system for monitoring a level of a gaseous molecular species within a flow of breathable gas. The system comprises means for emitting mid-infrared electromagnetic radiation; means for emitting near-infrared electromagnetic radiation; means for combining emitted mid-infrared electromagnetic radiation and emitted near-infrared electromagnetic radiation into a coaxial beam; means for directing the coaxial beam across a flow path of the flow of breathable gas that communicates with an airway of a subject; means for dividing electromagnetic radiation in the coaxial beam that has traversed the flow path into first radiation that includes mid-infrared electromagnetic radiation and second radiation that includes near-infrared electromagnetic radiation; means for generating output signals conveying information related to a parameter of the mid-infrared electromagnetic radiation in the first radiation; means for generating output signals conveying information related to a parameter of the near-infrared electromagnetic radiation in the second radiation; and means for determining a level of a gaseous molecular species within the flow of breathable gas in the flow path based on the output signals generated by the first radiation sensor and the second radiation sensor such that the output signals generated by the second radiation sensor are implemented to compensate optical loss through the flow path.

These and other objects, features, and characteristics of the present displosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
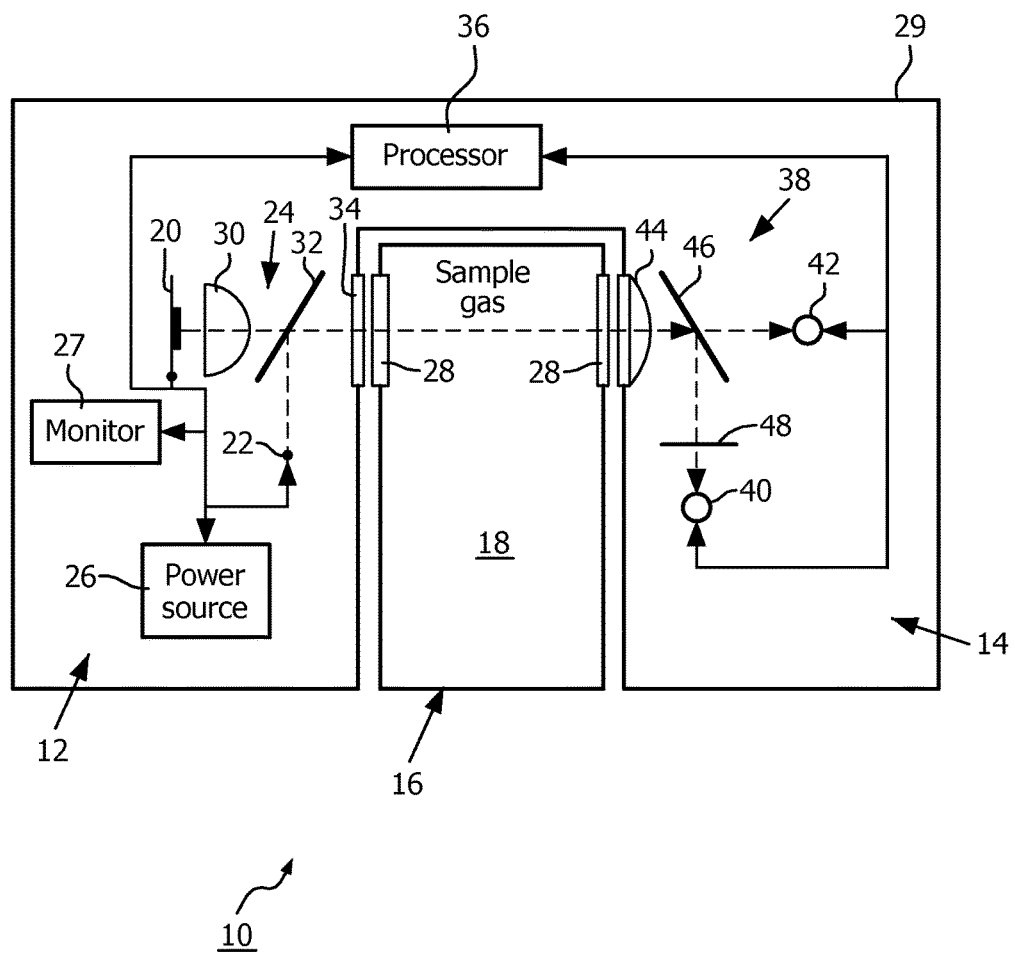
FIG. 1 illustrates a detector configured to measure a level of a gaseous molecular species in a flow of breathable gas.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a detector 10 configured to measure a level of a gaseous molecular species in a flow of breathable gas. The gaseous molecular species may be carbon dioxide, nitrous oxide, water vapor, anesthetic gas, and/or other gaseous molecular species. For convenience, particular reference is made below to measurement of carbon dioxide. It will be appreciated that such references are not limiting, and that the principles described with respect to the measurement of carbon dioxide could be practiced in the measurement of other gaseous molecular species without departing from the scope of this disclosure. Further, description herein of detector 10 being configured to measure the level of a gaseous molecular species in a respiratory therapy context is not limiting. The principles described herein are equally applicable to other systems that perform gas level measurement in other contexts (e.g., air quality detectors, automobile emissions detectors, and/or other systems).

In one embodiment, detector 10 includes a "U" shaped housing 29 enclosing a source assembly 12, a radiation sensor assembly 14, and/or other components. Two opposing legs of the "U" shaped housing 29 define opposite sides of a gap therebetween, with the source assembly 12 disposed in one leg on one side of the gap (source side) and the radiation sensor assembly 14 disposed in the opposing leg on the opposite side of the gap (detector side). A hollow airway assembly 16 can be removably docked in the U between the opposing legs. Detector 10 also includes self-contained electronics (some of which are shown in FIG. 1 and described below) disposed within the housing 29.

Airway assembly 16 forms a flow path 18 for a flow of breathable gas that communicates with the airway of a subject. Airway assembly 14 has windows 28 disposed on opposite sides such that infrared radiation entering flow path 18 via window 28 on one side of airway assembly 16 passes through the flow of breathable gas (patient respiration) in airway assembly 16 and exits via window 28 on the opposite side. Airway assembly 14 may be either a disposable unit or a reusable unit that removably clips into the gap in "U" shaped housing 29, with source assembly 12 and radiation sensor assembly 14 being generally arranged such that infrared radiation emanating from source assembly 12 is directed across the gap through the gas sample in airway assembly 16 to impinge upon radiation sensor assembly 14. The airway windows 28 may be formed of plastic film (disposable version), sapphire (reusable version) and/or other materials.

Source assembly 12 includes a first radiation source 20, a second radiation source 22, source optics 24, a power source 26, a source monitoring apparatus 27, and/or other components. First radiation source 20 is configured to emit broadband radiation including mid-infrared electromagnetic radiation. Infrared radiation generally refers to radiation occupying a band of wavelengths in the optical spectrum between 0.7 μm and 300 μm. Mid-infrared may generally refer to a mid-wavelength subset of the infrared radiation band between 3 μm and 8 μm. Mid-infrared radiation emitted by first radiation source 20 includes a gas wavelength ($\lambda_{GAS}$), at which radiation is absorbed by a gaseous molecular species of interest. The gaseous molecular species may include carbon dioxide, nitrous oxide, water vapor, anesthetic gases, and/or other gaseous molecular species. The radiation source 18 may operate substantially as a blackbody for at least a portion of the spectrum.

Second radiation source 22 is configured to emit electromagnetic radiation including near-infrared electromagnetic radiation. Near-infrared electromagnetic radiation may generally refer to a short-wavelength subset of the infrared radiation band between, for example, 0.7 μm and 3 μm. Sources that emit electromagnetic radiation in this range may be relatively inexpensive, power efficient, and rugged. For example, second radiation source 22 may include a light emitting diode, laser diode, and/or other sources.

Source optics 24 are configured to combine mid-infrared electromagnetic radiation emitted by first radiation source 20 and near-infrared electromagnetic radiation emitted by second radiation source 22 into a coaxial beam. Source optics 24 are configured to direct the coaxial beam across flow path 18 formed by airway assembly 14. Source optics 24 may include a lens 30, a beam combiner 32, a window 34, and/or other components. Lens 30 may be a sapphire half-ball lens that gathers and collimates the emitted radiation from first radiation source 20, directing it toward beam combiner 32. Beam combiner 32 is configured to combine electromagnetic radiation emitted by first radiation source 20 and electromagnetic radiation emitted by second radiation source 22 into the coaxial beam. The coaxial beam is directed from beam combiner 32 across the gap and through the airway assembly 16 towards the radiation sensor assembly 14 via window 32. The electromagnetic radiation is combined into a coaxial beam so that any materials present in flow path 18 will be in the path of the electromagnetic radiation emitted by first radiation source 20 and the electromagnetic radiation emitted by second radiation source 22.

Power source 26 may be configured to provide power to first radiation source 20, second radiation source 22, and/or other components. Power source 26 may include, for example, a battery, a capacitor, a power converter, a port or connector configured to receive power from an external source (e.g., a wall socket, a monitor, and/or other external power sources), and/or other sources of power. In some embodiments, power source 26 is configured to deliver power in a pulsed manner, in order to cause the radiation emitted by first radiation source 20 to be pulsed. To accomplish this, power source 26 may vary the potential, current, power, and/or other parameters of the electrical power provided to first radiation source 20. In one embodiment, the power is provided to first radiation source 20 such that first radiation source 20 is pulsed at about 100 Hz to produce a periodically varying mid-infrared signal with a period of about 10 milliseconds.

The source monitoring apparatus 27 is configured to generate output signals conveying information related to one or more parameters of power through first radiation source 20. Such parameters may include, for example, current, potential, power, resistance, induction, and/or other parameters. In some embodiments, the resistance through first radiation source 20 is of particular interest. As such, the one or more parameters may include resistance itself, and/or other parameters from which resistance through first radiation source 20 can be determined. The source monitoring apparatus 27 may be integrated with power source 26 and/or first radiation source 20, or may be formed separately as illustrated in FIG. 1.

A processor 36 is configured to provide information processing capabilities in detector 10. As such, processor 36 may include one or more of a digital processor, an analog processor, a digital circuit designed to process information, an analog circuit designed to process information, a state machine, and/or other mechanisms for electronically processing information. Although processor 36 is shown in FIG. 1 as a single entity, this is for illustrative purposes only. In some implementations, processor 36 may include a plurality of processing units. These processing units may be physically located within the same device, or processor 36 may represent processing functionality of a plurality of devices operating in coordination. The operation of processor 36 is discussed further below. The illustration of processor 36 as being included within detector 10 is not intended to be limiting. Some or all of the functionality attributed herein to processor 36 may be provided by one or more components disposed outside of detector 10.

Radiation sensor assembly 14 includes sensor optics 38, a first sensor 40, a second sensor 42, and/or other components. Sensor optics 38 are configured to direct electromagnetic radiation that has passed through flow path 18 formed by airway assembly 16 onto first sensor 40 and second sensor 42. In some embodiments, sensor optics 38 comprise a lens assembly 44, a beam splitter assembly 46, and/or other optical components. Lens assembly 44, which in one embodiment includes an AR-coated (Anti-Reflective coated) silicon plano-convex lens, focuses the infrared radiation reaching it from the source assembly 12, and directs the electromagnetic radiation toward first sensor 40 and second sensor 42 via beam splitter assembly 46. In beam splitter assembly 46, a dichroic beam-splitter is positioned to reflect mid-infrared radiation containing the molecular species of interest wavelength $\lambda_{GAS}$ towards first sensor 40, and to pass near infrared electromagnetic radiation towards second sensor 42. A narrow-band first optical filter 48 that passes $\lambda_{GAS}$ is positioned in front of first sensor 40. First sensor 40 generates output signals conveying information related to intensity and/or other parameters of the mid-infrared electromagnetic radiation that becomes incident thereon. First sensor 40 may include, for example, a PbSe substrate, a pyrometer, a thermopile, and/or other sensor devices. Second sensor 42 is configured to generate output signals conveying information related to intensity and/or other parameters of the near-infrared electromagnetic radiation that becomes incident thereon. Second sensor 42 may include, for example, a photodiode, such as InGaAs or Ge, or other sensor device. The sensor device included in second sensor 42 may be less costly, more rugged, and/or different in other ways from the sensor device included in first sensor 40. This may enhance detector 10 with respect to conventional detectors, which usually require two devices capable of detecting electromagnetic radiation within the mid-infrared range.

The basic principle of operation behind Capnometry/Capnography and/or detection of other gaseous molecular species via detector 10 is that infrared radiation in a band around an absorption wavelength for a gaseous molecular species of interest (e.g., 4.275 µm for carbon dioxide) experiences increasing absorption (when traveling a fixed-length path through a sample gas) with increasing concentration of the gaseous molecular species—according to a reliably repeatable relationship. On the other hand, the absorption near-infrared radiation under the same conditions is essentially unaffected by the molecular species of interest.

When the coaxial beam of electromagnetic radiation from source assembly 12 passes through the body of gas in airway assembly 14, mid-infrared radiation at $\lambda_{GAS}$ is attenuated according to the concentration of the molecular species of interest in the body of gas. Electromagnetic radiation in the near-infrared range, however, is unaffected by any such molecular species of interest in the body of gas. Therefore, changes in intensity of the mid-infrared electromagnetic radiation at $\lambda_{GAS}$ that has traversed flow path 18 without an accompanying drop in intensity of the near-infrared electromagnetic radiation that has traversed flow path 18 indicates absorption of the mid-infrared electromagnetic radiation by the gaseous molecular species. On the other hand, optical loss within flow path 18 that impacts both the mid-infrared and the near-infrared range indicates the presence of a substance (e.g., water condensation or droplets and/or other substances) that has scattered or blocked the electromagnetic radiation in both the near-infrared and mid-infrared ranges. As such, the intensity (or related parameter(s)) of electromagnetic radiation in the near-infrared range are used to normalize the intensity (or related parameter(s)) of electromagnetic radiation in the mid-infrared range to discern between absorption by the molecular species of interest and optical loss to scattering or blockage within flow path 18. The implementation in this manner of near-infrared electromagnetic radiation as a reference, rather than another wavelength in the mid-infrared range, may facilitate more robust compensation for optical loss within flow path 18.

Aside from optical loss within flow path 18, intensity (or related parameter(s)) of the mid-infrared electromagnetic radiation received at sensor assembly 14 may be impacted by fluctuations in irradiance of first source 20. However, such fluctuations tend to coincide with corresponding fluctuations in temperature of first radiation source 20. Temperature of first radiation source 20 may be determined as a function of electrical resistance through first radiation source 20. As such, the output signals generated by source monitoring apparatus 27 facilitate compensation for fluctuations in irradiance of first radiation source 20 in determining the level of the gaseous molecular species within flow path 18 based on the output signals generated by first sensor 40. For example, irradiance may be determined as a function of resistance through first radiation source 20, potential across first radiation source 20, current through first radiation source 20, and/or other parameters.

Processor 36 is configured to determine a level of a gaseous molecular species within the flow of breathable gas in the flow path based on the output signals generated by first sensor 40 and second sensor 42. This includes implementing the output signals generated by second sensor 42 to compensate for optical loss through flow path 18. Processor 36 is further configured to determine the level of the gaseous molecular species based on the output signals generated by source monitoring apparatus 27. This effectively adjusts the level determination for the irradiance of first radiation source 20. Processor 36 may be configured to determine the level of the gaseous molecular species based on the output signals of first sensor 40, second sensor 42, and/or source monitoring apparatus 27 with one or more of a function in which output signals are implemented as variable inputs, a look-up table, and/or through other computational techniques.

Figure 2:
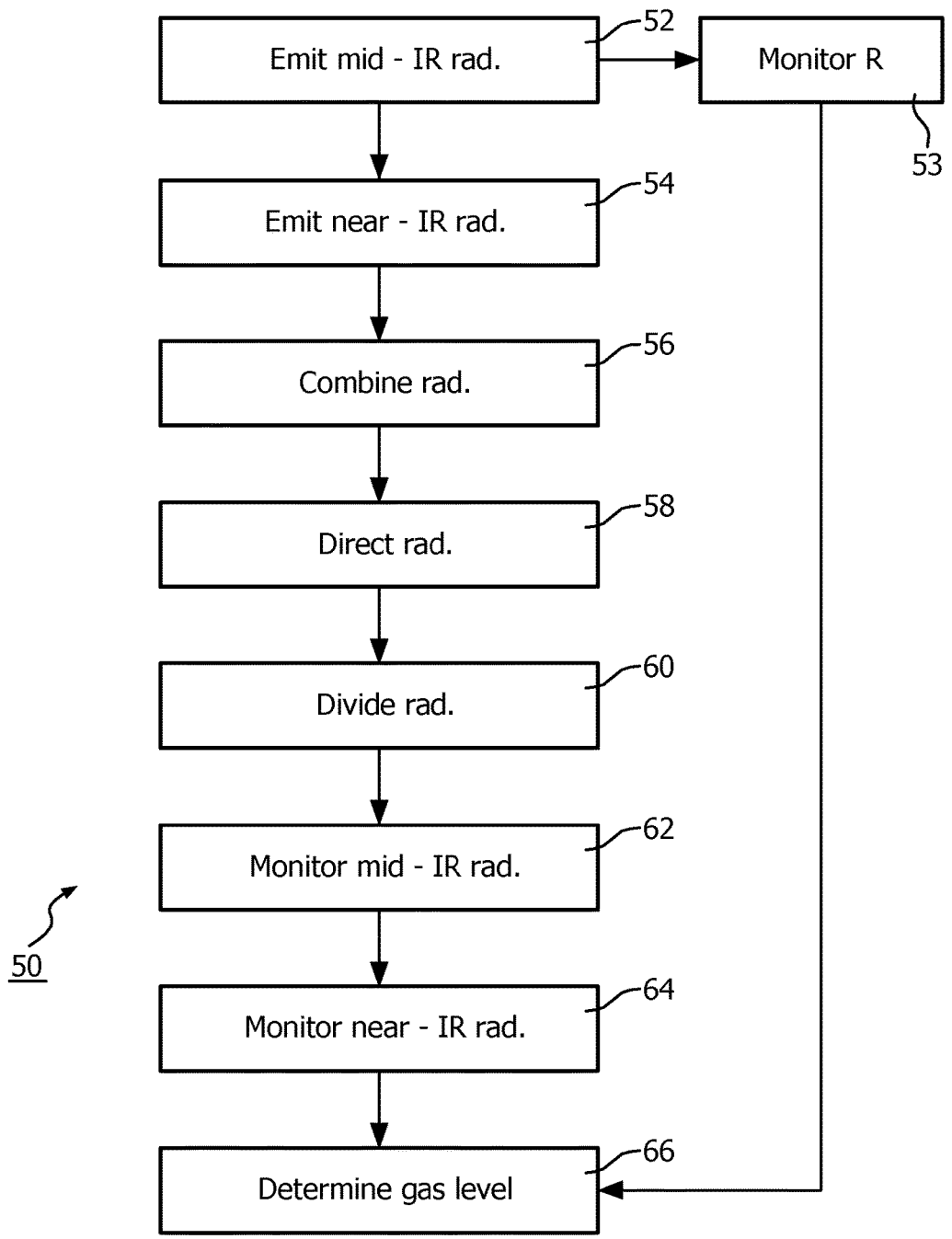
FIG. 2 illustrates a method of measuring a level of gaseous molecular species in a flow of breathable gas.

FIG. 2 illustrates a method 50 of monitoring a level of a gaseous molecular species within a flow of breathable gas. The operations of method 50 presented below are intended to be illustrative. In some embodiments, method 50 may be accomplished with one or more additional operations not described, and/or without one or more of the operations discussed. Additionally, the order in which the operations of method 50 are illustrated in FIG. 2 and described below is not intended to be limiting. In some embodiments, method 50 may be implemented in a detector similar to or the same as detector 10 (shown in FIG. 1 and described herein).

At an operation 52, mid-infrared electromagnetic radiation is emitted. In some embodiments, operation 52 is performed by a first radiation source the same as or similar to first radiation source 20 (shown in FIG. 1 and described herein).

At an operation 53, output signals conveying information related to electrical resistance through the first source are generated. In some embodiments, operation 53 is performed by a source monitoring apparatus the same as or similar to source monitoring apparatus 27 (shown in FIG. 1 and described herein).

At an operation 54, near-infrared electromagnetic radiation is emitted. In some embodiments, operation 54 is performed by a second radiation source the same as or similar to second radiation source 22 (shown in FIG. 1 and described herein).

At an operation 56, mid-infrared electromagnetic radiation emitted at operation 52 and near-infrared electromagnetic radiation emitted at operation 54 are combined into a coaxial beam. In some embodiments, operation 56 is performed by source optics the same as or similar to source optics 24 (shown in FIG. 1 and described herein).

At an operation 58, the coaxial beam is directed across a flow path of the flow of breathable gas that communicates with an airway of the subject. In some embodiments, operation 58 is performed by source optics the same as or similar to source optics 24 (shown in FIG. 1 and described herein).

At an operation 60, electromagnetic radiation in the coaxial beam that has traversed the flow path is divided into first radiation that includes mid-infrared electromagnetic radiation and second radiation that includes near-infrared electromagnetic radiation. In some embodiments, operation 60 is performed by sensor optics the same as or similar to sensor optics 38 (shown in FIG. 1 and described herein).

At an operation 62, output signals conveying information related to a parameter of the mid-infrared electromagnetic radiation in the first radiation are generated. In some embodiments, operation 62 is performed by a first sensor the same as or similar to first sensor 40 (shown in FIG. 1 and described herein).

At an operation 64, output signals conveying information related to a parameter of the near-infrared electromagnetic radiation in the second radiation are generated. In some embodiments, operation 64 is performed by a second sensor the same as or similar to second sensor 42 (shown in FIG. 1 and described herein).

At an operation 66, a level of gaseous molecular species within the flow of breathable gas is determined. The level determination may be made based on the output signals generated at one or more of operation 62, operation 64, and/or 53. Determination of the level of the gaseous molecular species based on the output signals generated at operation 64 compensates for optical loss through the flow path. Determination of the level of the gaseous molecular species based on the output signals generated at operation 53 effectively adjusts the level determination for the irradiance of the first source. In some embodiments operation 66 is performed by a processor the same as or similar to processor 36 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A detector configured to monitor a level of a gaseous molecular species within a flow of breathable gas, the detector comprising:

a first source configured to emit mid-infrared electromagnetic radiation;

a second source configured to emit near-infrared electromagnetic radiation;

source optics configured to combine mid-infrared electromagnetic radiation emitted by the first source and near-infrared electromagnetic radiation emitted by the second source into a coaxial beam, and to direct the coaxial beam across a flow path of a flow of breathable gas that communicates with an airway of a subject;

sensor optics configured to receive electromagnetic radiation in the coaxial beam that has traversed the flow path, and to divide the received electromagnetic radiation into first radiation that includes mid-infrared electromagnetic radiation and second radiation that includes near-infrared electromagnetic radiation;

a first radiation sensor configured to receive the first radiation, and to generate output signals conveying information related to a parameter of the mid-infrared electromagnetic radiation in the first radiation;

a second radiation sensor configured to receive the second radiation, and to generate output signals conveying information related to a parameter of the near-infrared electromagnetic radiation in the second radiation; and a processor configured to determine a level of a gaseous molecular species within the flow of breathable gas in the flow path based on the output signals generated by the first radiation sensor and the second radiation sensor such that the output signals generated by the second radiation sensor are implemented to compensate optical loss through the flow path;

wherein the gaseous molecular species is carbon dioxide, nitrous oxide, water vapor, or anesthetic gas.

2. The detector of claim 1, further comprising a source monitoring apparatus configured to generate output signals conveying information related to electrical resistance through the first source, and wherein the processor is further configured such that the determination of the level of the gaseous molecular species is further based on the output signals generated by the source monitoring apparatus to account for the electrical resistance through the first source.

3. The detector of claim 2, wherein determining the level of the gaseous molecular species based on the output signals generated by the source monitoring apparatus effectively adjusts the level determination for the irradiance of the first source.

4. The detector of claim 1, wherein the second radiation sensor includes a photodiode.

5. The detector of claim 4, wherein the first radiation sensor includes a PbSe substrate, a pyrometer, or a thermopile.

6. The detector of claim 5, wherein the second radiation sensor includes the photodiode comprising an InGaAs or Ge photodiode.

7. The detector of claim 1, wherein the second source includes at least one of a light emitting diode or a laser diode.

8. The detector of claim 1, wherein:
the first radiation sensor is configured to generate the output signals conveying information related to an intensity of the mid-infrared electromagnetic radiation in the first radiation;
the second radiation sensor is configured to generate the output signals conveying information related to an intensity of the near-infrared electromagnetic radiation in the second radiation; and
the processor is configured to determine the level of the gaseous molecular species within the flow of breathable gas in the flow path based on the output signals generated by the first radiation sensor and the second radiation sensor including normalizing the intensity of the mid-infrared electromagnetic radiation in the first radiation using the intensity of the near-infrared electromagnetic radiation in the second radiation to compensate optical loss through the flow path.

9. A method of monitoring a level of a gaseous molecular species within a flow of breathable gas with a detector that includes a first source, a second source, source optics, sensor optics, a first radiation sensor, a second radiation sensor, and a processor, the method comprising:

emitting mid-infrared electromagnetic radiation from the first source;

emitting near-infrared electromagnetic radiation from the second source;

combining, with the source optics, mid-infrared electromagnetic radiation emitted by the first source and near-infrared electromagnetic radiation emitted by the second source into a coaxial beam;

directing, with the source optics, the coaxial beam across a flow path of the flow of breathable gas that communicates with an airway of a subject;

dividing, with the sensor optics, electromagnetic radiation in the coaxial beam that has traversed the flow path into first radiation that includes mid-infrared electromagnetic radiation and second radiation that includes near-infrared electromagnetic radiation;

generating, with the first radiation sensor, output signals conveying information related to a parameter of the mid-infrared electromagnetic radiation in the first radiation;

generating, with the second radiation sensor, output signals conveying information related to a parameter of the near-infrared electromagnetic radiation in the second radiation; and determining, by the processor, a level of a gaseous molecular species within the flow of breathable gas in the flow path based on the output signals generated by the first radiation sensor and the second radiation sensor such that the output signals generated by the second radiation sensor are implemented to compensate optical loss through the flow path.

10. The method of claim 9, wherein the detector further includes a source monitoring apparatus, wherein the method further comprises generating, with the source monitoring apparatus, output signals conveying information related to electrical resistance through the first source, and wherein the determination of the level of the gaseous molecular species is further based on the output signals generated by the source monitoring apparatus to account for the electrical resistance through the first source.

11. The method of claim 10, wherein determining the level of the gaseous molecular species based on the output signals generated by the source monitoring apparatus effectively adjusts the level determination for the irradiance of the first source.

12. The method of claim 9, wherein the second radiation sensor includes a photodiode.

13. The method of claim 9, wherein the second source includes at least one of a light emitting diode or a laser diode.

14. The method of claim 9, wherein:
the output signals conveying information related to a parameter of the mid-infrared electromagnetic radiation in the first radiation include output signals conveying information related to an intensity of the mid-infrared electromagnetic radiation in the first radiation;
the output signals conveying information related to a parameter of the near-infrared electromagnetic radiation in the second radiation include output signals conveying information related to an intensity of the near-infrared electromagnetic radiation in the second radiation; and
the level of the gaseous molecular species within the flow of breathable gas in the flow path is determined based on the output signals generated by the first radiation sensor and the second radiation sensor including normalizing the intensity of the mid-infrared electromagnetic radiation in the first radiation using the intensity of the near-infrared electromagnetic radiation in the second radiation to compensate optical loss through the flow path.

15. The method of claim 9, wherein the gaseous molecular species is carbon dioxide, nitrous oxide, or water vapor.

16. A detector configured to monitor a level of a gaseous molecular species within a flow of breathable gas, the system comprising:
a first source configured to emit mid-infrared electromagnetic radiation;
a second source configured to emit near-infrared electromagnetic radiation;
source optics configured to combine mid-infrared electromagnetic radiation emitted by the first source and near-infrared electromagnetic radiation emitted by the second source into a coaxial beam directed across a flow path of the flow of breathable gas that communicates with an airway of a subject;
sensor optics configured to divide electromagnetic radiation in the coaxial beam that has traversed the flow path into first radiation that includes mid-infrared electromagnetic radiation and second radiation that includes near-infrared electromagnetic radiation;
a first radiation sensor configured to receive the first radiation and to generate output signals conveying information related to a parameter of the mid-infrared electromagnetic radiation in the first radiation;
a second radiation sensor configured to receive the second radiation and to generate output signals conveying information related to a parameter of the near-infrared electromagnetic radiation in the second radiation; and
a processor configured to determine a level of carbon dioxide within the flow of breathable gas in the flow path based on the output signals generated by the first radiation sensor and the second radiation sensor such that the output signals generated by the second radiation sensor are implemented to compensate optical loss through the flow path.

17. The detector of claim 16, further comprising:
a source monitoring apparatus configured to generate output signals conveying information related to electrical resistance through the first source,
wherein the processor is further configured such that the determination of the level of carbon dioxide is further based on the output signals generated by the source monitoring apparatus to account for the electrical resistance through the first source.

18. The detector of claim 17, wherein determining the level of carbon dioxide based on the output signals generated by the source monitoring apparatus effectively adjusts the level determination for the irradiance of the first source.

19. The detector of claim 16, wherein the second radiation sensor includes a photodiode.

20. The detector of claim 16, wherein the second source includes at least one of a light emitting diode or a laser diode.

* * * * *